Figure 1:
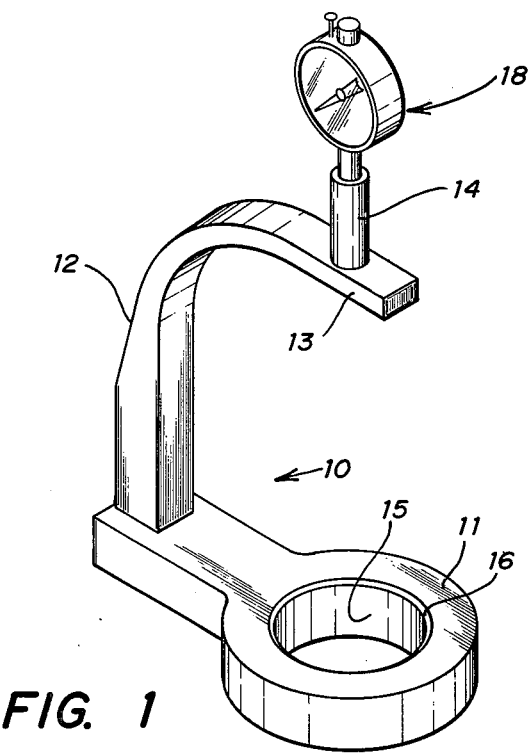

United States Patent [19]

Hejkal

[11] 4,116,047
[45] Sep. 26, 1978

[54] BOWLING BALL AND HARDNESS MEASURING INSTRUMENT HOLDING DEVICE

[76] Inventor: Charles S. Hejkal, 617 W. Commerce St., Dallas, Tex. 75208

[21] Appl. No.: 830,677

[22] Filed: Sep. 6, 1977

[51] Int. Cl.² .............................................. G01N 3/42
[52] U.S. Cl. ...................................................... 73/81
[58] Field of Search ...................................... 73/81, 78

[56] References Cited

U.S. PATENT DOCUMENTS

| | | | |
|---|---|---|---|
| 1,037,596 | 9/1912 | Coppage | 73/81 |
| 1,661,718 | 3/1928 | Davis | 73/81 |
| 1,890,923 | 12/1932 | Wilson | 73/81 |
| 2,278,416 | 4/1942 | Atti | 73/94 |
| 2,421,449 | 6/1947 | Zuber | 73/81 |
| 3,088,591 | 5/1963 | Perthen et al. | 73/78 X |
| 3,376,734 | 4/1968 | Ether | 73/78 |
| 3,470,737 | 10/1969 | Fridley | 73/81 |
| 3,478,568 | 11/1969 | Borgersen | 73/81 |

FOREIGN PATENT DOCUMENTS

| | | | |
|---|---|---|---|
| 2,249,325 | 4/1973 | Fed. Rep. of Germany | 73/81 |
| 337,018 | 4/1959 | Switzerland | 73/81 |

*Primary Examiner*—Herbert Goldstein
*Attorney, Agent, or Firm*—Robert G. Boydston

[57] ABSTRACT

A holding device having positioning means in a horizontal base member to support and position a generally spherical test object in alignment with a hardness measuring instrument positioned by retaining means in a base member connected upright member extended radially over the test object.

2 Claims, 4 Drawing Figures

U.S. Patent   Sept. 26, 1978   4,116,047

BOWLING BALL AND HARDNESS MEASURING INSTRUMENT HOLDING DEVICE

This invention relates in general to test object and instrument holding devices and in particular to a holding device for generally spherically shaped objects during measurement for hardness of the material of composition. The holding device is particularly useful for positioning and holding a bowling ball for hardness measuring with an instrument designed for hand held use.

Bowling is a popular, world-wide recreational sport today. Millions of people participate regularly in friendly competition for prizes and prestige in amateur leagues and tournaments. Professional bowlers compete for prizes that determine their individual livelihoods. Rules for the sport and for the equipment used are promulgated by the American Bowling Congress for amateurs and by the Professional Bowlers Association for the professionals.

In bowling, a ball is rolled from one end down the length of a proscribed boundary known as an "alley" or "lane". At the other end of the alley is an upright group of ten wooden pins arranged in an equilaterally triangular pattern. This pattern is formed by four rows of pins, each succeeding row of pins having one more pin than its predecessor. The apex of the triangle is in the lateral center of the alley and is formed by one row of one pin. This pin, if the ball is rolled accurately, would be the first struck by the ball and is called the "head pin". The base of the triangle is perpendicular to the side boundaries of the alley and is formed by one row of four pins. The object of the game is to topple a maximum number of pins in an allotted number of ball rolls.

As the ball strikes one or more pins, the struck pin or pins are thrust away from the ball due to the elasticity of the ball and pins and momentum imparted by the velocity and greater weight of the ball. The struck pins must move so as to topple other pins for the bowler to score well. This movement of struck pins is known as "pin action".

The advent of plastic bowling balls having a softer material composition than the formerly used hard rubber balls made hardness standards necessary to the rules of the game. Being more elastic than hard rubber, the softer plastic bowling balls can impart greater speed and different directions to the struck pins. Thus, pins struck by a relatively soft plastic ball scatter more widely and tumble more violently resulting in more pin action and higher scores. Minimum ball hardness standards have been established for bowling balls used by participants thereby making the participant's score principally dependent on skill rather than elasticity of the ball.

It is known that testing for the hardness of a material of any shape may be accomplished by use of a standard hardness measuring device comprises of a metered gauge and a shaft joined to coil springs with one end of the shaft contacting the indicator in the gauge and the other end pointed to form a test prod. The shaft and springs combination is encased within a sleeve which is rigidly connected at one end to the metered gauge encasement. The tension of the spring combination causes the prod end of the shaft to extend beyond the outer end of the sleeve in a balanced floating position when the measuring device is not in use. To measure the material hardness of an object, the pointed shaft test prod and outer end of the sleeve are pressed perpendicularly against the material's surface thereby forcing the shaft back into the sleeve. The gauge indication depends upon how deeply the prod end of the shaft depresses the material undergoing measurement; that is, upon the extent to which the surface of the material yields to the pressure of the spring-loaded shaft prod end.

Accurate and consistent measurements are obtained only when the measuring device is applied exactly perpendicular to the surface of the object being tested. When not applied perpendicularly, the potential travel distance of the prod ended shaft is limited to less than that for which the springs are calibrated. Also, lateral force may be imposed on the prod resulting in fricton between the shaft and sleeve that would falsely show on the gauge reading as resistance to yield due to hardness of the material being tested. In a hardness measuring instrument having springs calibrated for relatively soft, compressible materials, the error thus introduced into the gauge reading is of considerable significance. Any lateral force imposed on the test prod may also damage the instrument. It is extremely difficult to apply a hand held hardness measuring instrument of this type exactly perpendicular to the tangential plane of a spherical test object surface as required to obtain accurate and consistent hardness measurements and to avoid instrument damage.

The commonly used hardness measuring instrument is of typical design generally described in U.S. Pat. No. 2,421,449, issued June 3, 1947, John G. Zuber, Inventor, Class 73-31. At present, bowling balls are hardness tested by hand held application of the test instrument or by guiding the test instrument through a hand held positioning device. Often the test operator must use one hand to hold the ball stationary while applying the instrument with the other hand or must have assistance to coordinate the ball, guide device and hardness measuring instrument. Human error is invariably introduced by the operator's inability to apply the instrument in a truly perpendicular manner and the greater the operator's inexperience, the greater the probability of error.

In a typical bowling establishment, frequented daily by many participants, the demand for use of the establishment's hardness measuring instrument or instruments, coupled with the small size and substantial value of each instrument, may result in damage, loss or theft of instruments unless closely monitored by personnel employed by the establishment. Minimization of expense from employee time involved in ball hardness measuring and from instrument loss and damage is, of course, of economic importance to the bowling establishment.

It is, therefore, a principal object of this invention to provide a holding device to hold an object being measured for material hardness and a hardness measuring instrument in aligned positions for consistent and accurate hardness measurement results.

Another object is to provide a holding device for positioning and retaining generally spherically shaped objects in a place aligned with an instrument for hardness measuring.

A further object is to provide a hardness measuring holding device with instrument retaining means for a measuring instrument designed for hand held use whereby the errors resulting from hand held use are eliminated.

Still another object is to provide a standard bowling ball and hardness measuring instrument holding device for hardness measuring of bowling balls.

Features of the invention useful in accomplishing the above objects include, in a test object and instrument holding device, a rigid horizontal base member forming a platform stand having means for retaining the object being tested in a predetermined position, and an upright radially extended member rigidly connected to the base member and having a retaining means for positioning a test instrument directly over the object being hardness tested or measured. The test instrument retaining means is configured to position the test instrument directly over the center of a spherical test object, to positively retain and guide the test instrument during hardness measuring tests and to positively retain the instrument when it is not in use. The test instrument retaining means contains a spring means to retract the test instrument when not in use and when test objects are being moved within, to or from the test object and instrument holding device.

Figure 2:
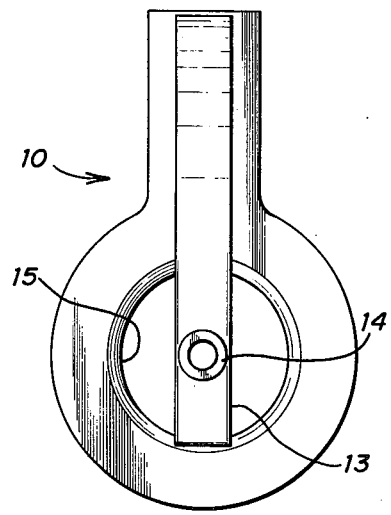
Figure 3:
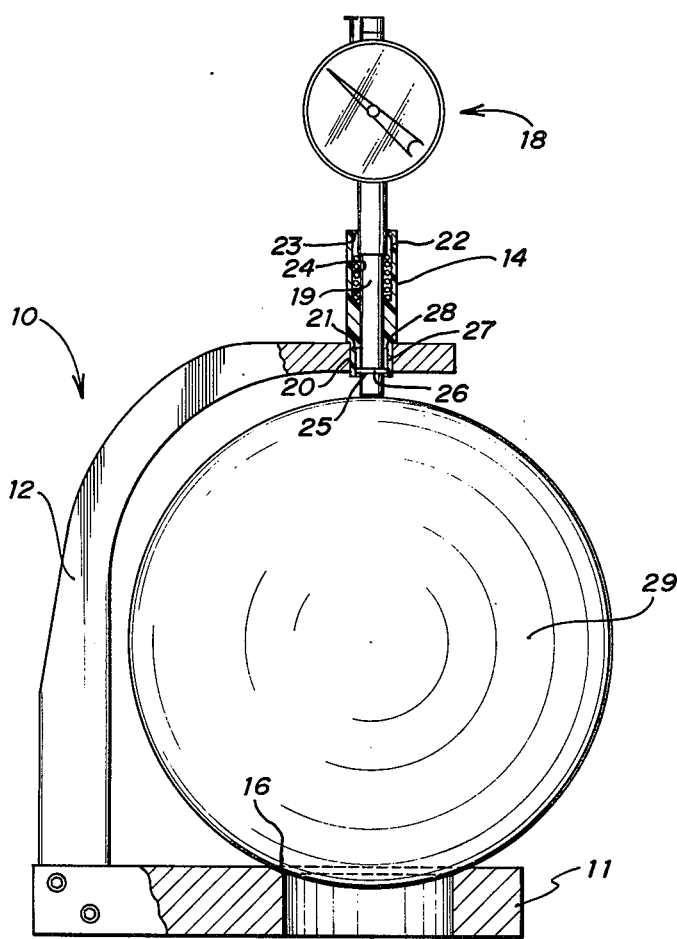
Figure 4:
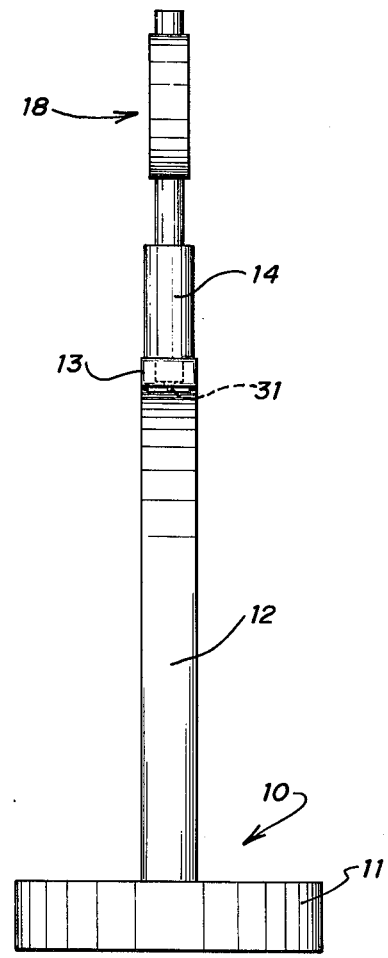

A specific embodiment, representing what is presently regarded as the best mode of carrying out the invention, is illustrated in the accompanying drawing:

In the drawing:

FIG. 1 represents a perspective view of the test object and instrument holding device with a hardness measuring instrument positioned in the test instrument retaining means of the radially extended upright member;

FIG. 2, a top plan view of the test object and instrument holding device;

FIG. 3, a side elevation view of the test object and instrument holding device, partially cross-sectioned, showing a spherical test object in proper position with a hardness measuring instrument in the use position against the surface of the test object, and;

FIG. 4, an end elevation view of the test object and instrument holding device with a hardness measuring instrument in the retracted or rest position in the instrument retaining means.

Referring to the drawing:

The test object and instrument holding device 10 of FIG. 1 is shown with horizontal base member 11 supporting rigidly connected or integral upright member 12 having a radially extended outer end 13 mounting a retaining means 14 for test instrument 18. The radially extended outer end 13 is parallel to base member 11 and is positioned so that the test instrument retaining means 14 is vertically concentric with the test object retaining means 15. This can be observed in FIG. 2, a top plan view of the test object and instrument holding device 10 having the test instrument retaining means 14 vertically centered over the test object retaining means 15.

In the preferred embodiment, the test object retaining means 15 takes the form of a bore through and perpendicular to the horizontal plane of base member 11. Additionally, in the preferred embodiment, the test object retaining means 15 includes a chamfer 16 providing additional seating surface, added support and retention of the spherical test object 29 as shown in FIG. 3.

The test instrument retaining means 14 of FIG. 3 comprises a tubular sleeve having a reduced outer diameter section 20 that fits tightly into a bore 21 through the radially extended outer end 13 of upright member 12. The tubular sleeve has a bore through, being of a sufficient diameter to allow the shaft sleeve 19 of the test instrument 18 passage through while guiding the shaft sleeve 19 in a vertically concentric attitude with a radius to the geometric center of the test object 29. Although a tubular sleeve having a straight through bore provides basic test instrument retaining means, the tubular sleeve in the preferred embodiment of FIG. 3 has a top counterbore chamber 24 and a bottom counterbore section 27 each of larger inside diameter than the intermediate portion of the tubular sleeve.

In the upper chamber 24, a coil spring 22 is stopped at the bottom of the chamber 24 by a shoulder formed by a smaller inside diameter intermediate portion of the tubular sleeve and is retained at the upper end of the chamber 24 by an annular shoulder 23. The inside diameter of the spring 22 is such that the larger outside diameter upper portion of instrument shaft sleeve 19 will not pass through the spring 22. When the test instrument 15 is manually pressed against the surface of the test object 29, as in FIG. 3, the coil spring 22 is compressed. When the manual force is released from the test instrument 15, the coil spring 22 will elongate, retracting the test instrument 14, as shown in FIG. 4, to the rest position. In that position, the hardness measuring instrument shaft sleeve 19 is retracted inside the instrument retaining means lower counterbore 27. Also, the instrument prob 31 that projects slightly beyond the end of the shaft sleeve 19 when the instrument 18 is not in use is retracted inside the counterbore 27 where neither prob 31 nor shaft sleeve 19 can interfere with or be damaged by a test object 29 being placed into or removed from the test object holding device 10.

A resilient material ferrule 26 such as a common rubber O-ring stretch fitted over the end of shaft sleeve 19 to firmly grip the shaft sleeve 19 in annular groove 25 moves axially within bottom counterbore section 27 with movement of the shaft sleeve 19 when the instrument 18 is manually pushed downward or forced upward by the coil spring 22. Upward movement or retraction of the instrument 18 is stopped at the optimum place of retraction when the ferrule 26 engages in an annular abuttment 28 at the upper end of section 27. Thus, accidental and intentional rapid manual withdrawal of the test instrument 18 from the test instrument retaining means 14 is prevented by the ferrule 26; and thereby, the potential for loss, damage, and theft of hardness measuring instruments is substantially reduced.

In the procedure of using this invention, the test object 29 is held by the retaining means 15 in a stationary position aligned with the hardness measuring instrument 18 that is positioned in the instrument retaining means 14. The operator has both hands free to depress the instrument 18 against the test object 29, reset the instrument gauge to the zero or rest position after observing the gauge indicator position and rotate the test object 29 to obtain another measurement at a different test object surface location. The procedure is easily repeated to obtain the desired number of measurements at different surface locations. The close clearance between the test instrument retaining means 14 intermediate bore portion located between upper chamber 24 and lower section 27 and the test instrument shaft sleeve 19 accurately guides the test instrument prob 31 to a perpendicular attitude with a tangential plane through the point of contact on the surface of the test object 29. Additional guiding effect is provided through close clearance between the shaft sleeve 19 and the upper end of the test instrument retaining means 14 that forms annular shoulder 23. Thus, the errors in measurment introduced when the hardness measuring instrument 18 is manually applied to the surface of a test object 29 without the use of this invention because of operator inability to hand hold and apply the instrument in true perpendicular alignment with a tangential plane through a surface contact point on a spherical test object are eliminated and consistent measurements are obtained.

Whereas this invention is herein illustrated and described with respect to a plurality of embodiments thereof, it should be realized that various changes may be made without departing from the essential contributions to the art made by the teachings hereof.

I claim:

1. In a bowling ball and hardness measuring instrument holding device, a platform base member having a vertical bore through and a chamfer at an upper end intersection of the bore with a platform base member top surface forming a bowling ball retaining means; an upright member affixed at an end of the platform base member and having a free end section with a through bore vertically concentric with the platform base member vertical bore, the free end section above and spaced from the platform base member a distance greater than a diameter of a bowling ball; a straight tubular sleeve having a greater outside diameter portion and a lesser outside diameter portion, the greater diameter portion projected perpendicularly above the upright member free end section and the lesser diameter portion tightly fitted into the free end section through bore; a coil spring return means within an inner cylindrical chamber of the tubular sleeve, the coil spring and tubular sleeve having suitable inside diameters concentric with the free end section vertical bore to facilitate guided axial passage of a shaft sleeve of a hardness measuring instrument to the extent where an upper end of the coil spring engages an annular shoulder of the shaft sleeve causing resilient compression of the coil spring with axial movement of the shaft sleeve by a manual downward force on the hardness measuring instrument, the force moving a hardness measuring instrument shaft sleeve probe end to contact a surface of a bowling ball in the bowling ball retaining means; the hardness measuring instrument shaft sleeve probe end retracted into the tubular sleeve by resiliency of the coil spring with the downward force removed from the hardness measuring instrument.

2. The device of claim 1, wherein within the lesser outside diameter portion of the tubular sleeve an inside annular shoulder is formed by an intersection of an inside diameter of an intermediate section with a larger inside diameter section extended through a lower end of said tubular sleeve, said inside annular shoulder providing upward axial travel limit stop when engaged by a ferrule on a hardness measuring instrument shaft sleeve.

* * * * *